US007277175B2

(12) United States Patent
Thompson et al.

(10) Patent No.: US 7,277,175 B2
(45) Date of Patent: Oct. 2, 2007

(54) SYSTEMS AND METHODS FOR WAVELENGTH SELECTIVE MEASUREMENT OF PROPERTIES OF SMALL VOLUME LIQUID SAMPLES

(75) Inventors: Judith A. Thompson, Wilmington, DE (US); John C. Kralik, Devon, PA (US)

(73) Assignee: Agilent Technologies, Inc., Santa Clara, CA (US)

( * ) Notice: Subject to any disclaimer, the term of this patent is extended or adjusted under 35 U.S.C. 154(b) by 286 days.

(21) Appl. No.: 10/946,209

(22) Filed: Sep. 21, 2004

(65) Prior Publication Data

US 2006/0061764 A1    Mar. 23, 2006

(51) Int. Cl.
*G01J 3/51* (2006.01)
(52) U.S. Cl. ............... 356/416; 356/418; 356/419; 356/414
(58) Field of Classification Search ............ 356/416, 356/417, 418, 419, 414
See application file for complete search history.

(56) References Cited

U.S. PATENT DOCUMENTS

| | | | |
|---|---|---|---|
| 3,659,945 A | 5/1972 | Roche et al. | |
| 3,963,351 A | 6/1976 | Chance et al. | |
| 4,171,909 A | 10/1979 | Kramer et al. | |
| 4,477,190 A | 10/1984 | Liston et al. | |
| 5,436,718 A * | 7/1995 | Fernandes et al. | 356/418 |
| 5,528,050 A * | 6/1996 | Miller et al. | 250/585 |
| 5,854,684 A * | 12/1998 | Stabile et al. | 356/440 |
| 6,002,488 A | 12/1999 | Berg et al. | |
| 6,542,241 B1 * | 4/2003 | Thorwirth et al. | 356/436 |
| 6,723,990 B2 | 4/2004 | DiDomenico et al. | |

OTHER PUBLICATIONS

"20D Spectrophotometer" Copyright 1996-2004 Motic®. Retrieved from http://www.motic.com/ap/eng/products/20d.html on Sep. 13, 2004.

Cairn Spectrophotometer Manual. Copyright 1996-1998 Cairn Research Ltd. Retrieved from http://www.cairnweb.com/manuals specman/contents.html on Sep. 14, 2004.

* cited by examiner

*Primary Examiner*—F. L. Evans

(57) ABSTRACT

A system for measuring properties of small volume liquid samples, where the system includes wavelength selective filters.

26 Claims, 3 Drawing Sheets

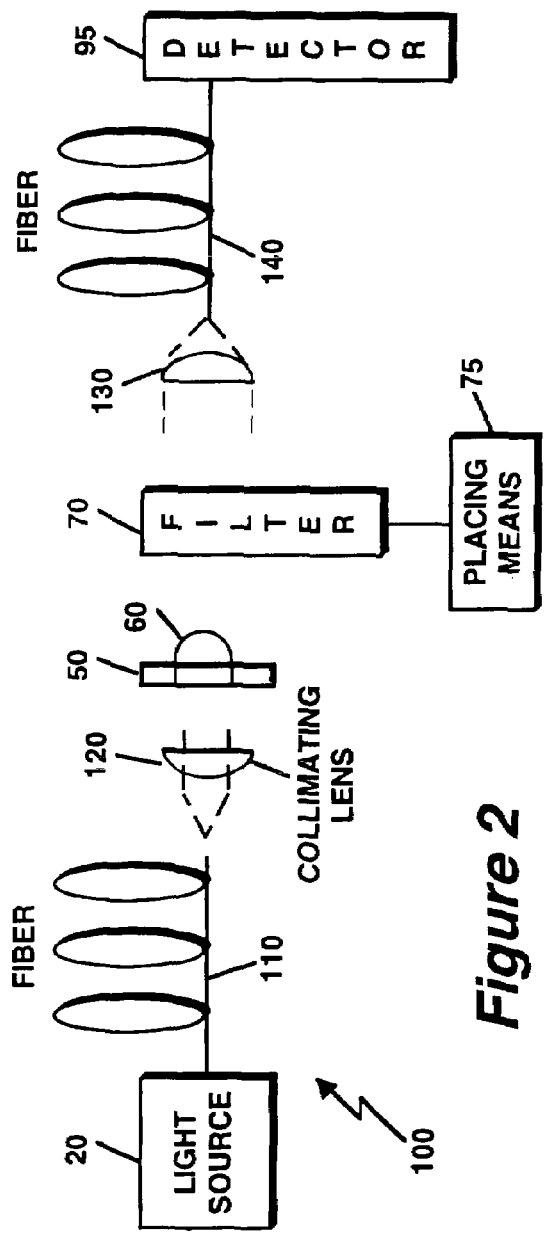
Figure 2
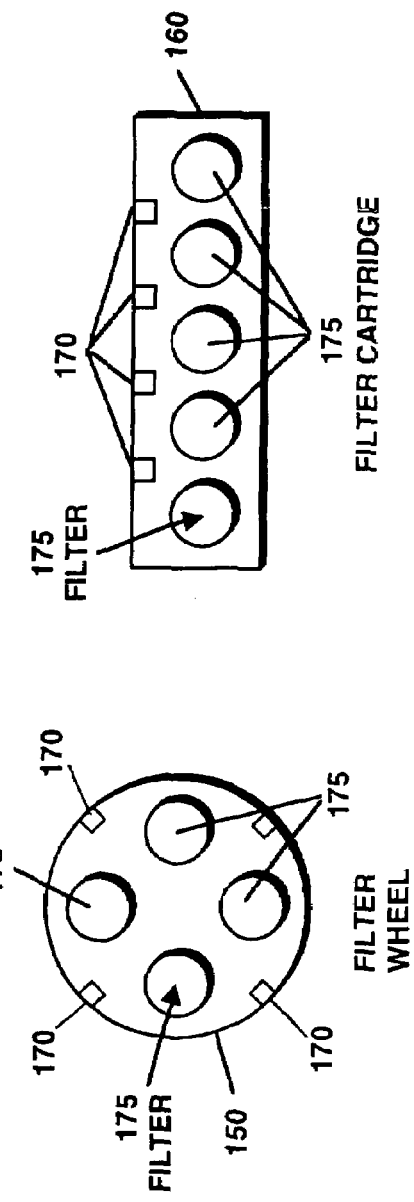
Figure 4
Figure 3

SYSTEMS AND METHODS FOR WAVELENGTH SELECTIVE MEASUREMENT OF PROPERTIES OF SMALL VOLUME LIQUID SAMPLES

BACKGROUND OF THE INVENTION

This invention relates generally to systems and methods for the measurement of properties of liquid samples.

Liquids, mixtures, solutions and reacting mixtures are often characterized using optical techniques such as photometry, spectrophotometry, fluorometry, or spectrofluorometry. In order to characterize samples of these liquids, the liquid is usually contained in a vessel referred to as a cell or cuvette, two or more of whose sides are of optical quality and permit the passage of those wavelengths needed to characterize the liquid contained therein. Recent applications require the characterization of very small liquid sample volumes. When dealing with very small sample volumes of, for example, from 1 to 2 microliters, it is difficult to create cells or cuvettes small enough to be filled and permit the industry standard 1 cm optical path to be used. The size of the cuvettes cannot be arbitrarily reduced since this results in increasing interference caused by the meniscus of the liquid, by the cuvette itself, by bubbles and other effects.

Several systems have been proposed to enable the measurement of very small liquid sample volumes. In one of the existing systems, a sample of the liquid to be examined is inserted, by means of a dispenser needle or other means, and retained between a light transmitter and a light receiver. In another one of the existing systems, the surface tension of a microliter or submicroliter sample of liquid is used to provide sufficient means to confine the sample between two substantially parallel surfaces on anvils spaced apart a known distance; two optical fibers penetrate the parallel surfaces and provide the light for the measurement.

It is desirable to insert a wavelength selective filter in the optical train in the vicinity of the measurement location in order to increase signal-to-noise. In the existing solutions described, a filter can not be inserted in the optical train in the vicinity of the measurement location.

There is, therefore, a need for a system for measuring properties of small volume liquid samples that allows the insertion of wavelength selective filters in the optical train in the vicinity of the measurement location.

There is a further need for a system that allows the insertion of selectable filters in the optical train in the vicinity of the measurement location.

BRIEF SUMMARY OF THE INVENTION

The needs for the invention set forth above as well as further and other needs and advantages of the present invention are achieved by the embodiments of the invention described hereinbelow.

In one aspect of this invention, a system for measuring properties of small volume liquid samples where the system design allows the insertion of wavelength selective filters in the optical train in the vicinity of the measurement location is disclosed.

The apparatus of this invention includes, for example, but not a limitation of this invention, a source of electromagnetic radiation, a first optical system, an optical delivery system capable of providing electromagnetic radiation from the source to the first optical system, where the first optical system is capable of substantially collimating the provided electromagnetic radiation, a sample holding assembly capable of holding a microvolume liquid sample and placing the microvolume liquid sample in an optical path of the substantially collimated electromagnetic radiation, a filter assembly comprising at least one filter, a second optical system capable of receiving electromagnetic radiation transmitted through the sample, at least a portion of the sample holding assembly and the filter assembly, an optical transmission system capable of receiving electromagnetic radiation from the second optical system and transmitting the received electromagnetic radiation to a detecting system, and the detecting system for detecting electromagnetic radiation.

For a better understanding of the present invention, together with other and further needs thereof, reference is made to the accompanying drawings and detailed description and its scope will be pointed out in the appended claims.

BRIEF DESCRIPTION OF THE SEVERAL VIEWS OF THE DRAWING

FIG. 2 is a schematic representation of yet another embodiment of the apparatus of this invention;

FIG. 3 is a schematic representation of an embodiment of a filter assembly of this invention;

FIG. 4 is a schematic representation of another embodiment of a filter assembly of this invention.

DETAILED DESCRIPTION OF THE INVENTION

A system, for measuring properties of small volume liquid samples, that allows the insertion of wavelength selective filters in the optical train in the vicinity of the measurement location is disclosed hereinbelow.

The term "microvolume" liquid sample as used herein refers to small sample volumes of about 20 microliters or less and typically 1 to 2 microliters or less.

Figure 1A:
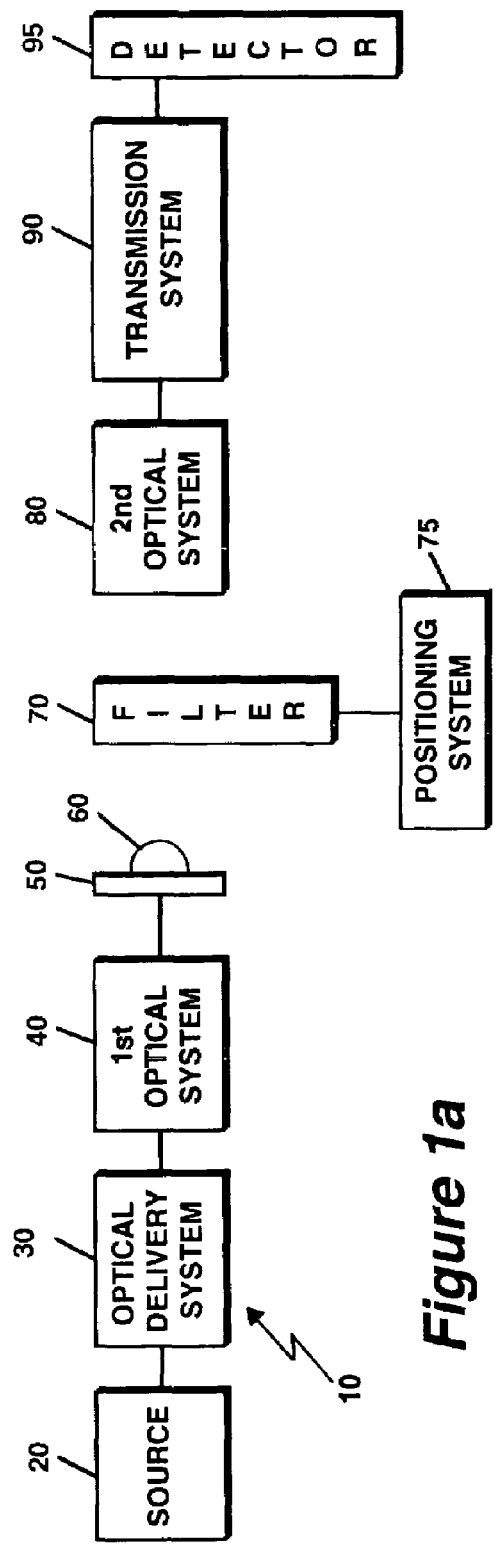
FIG. 1a is a schematic block diagram representation of an embodiment of the apparatus of this invention.
Figure 1B:
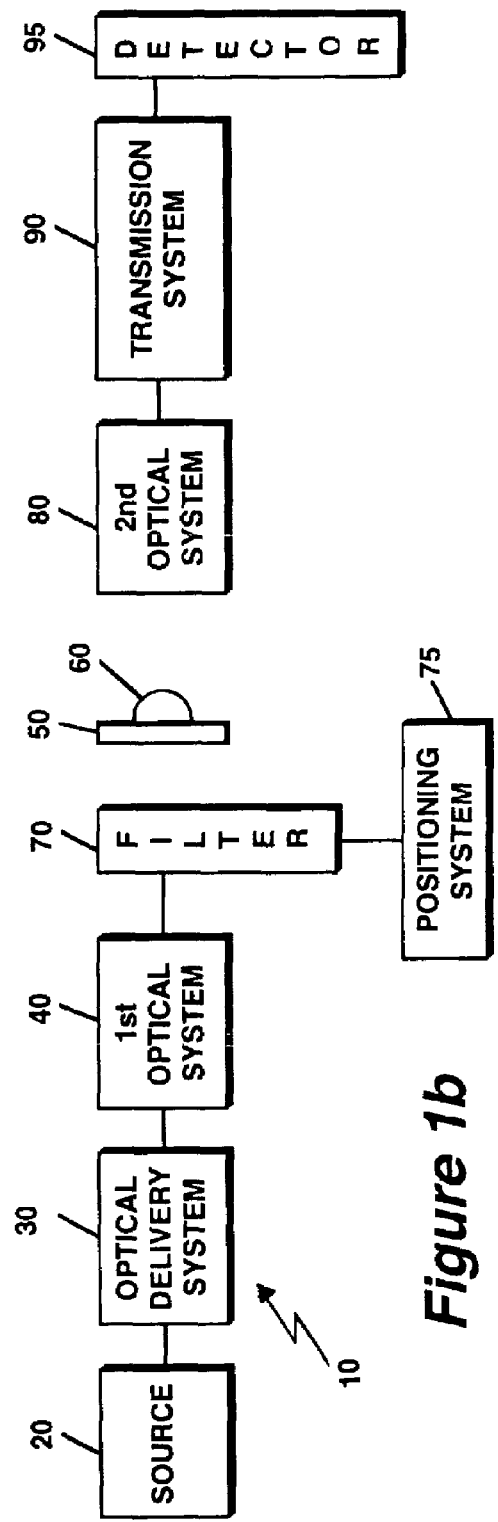
FIG. 1b is a schematic block diagram representation of another embodiment of the apparatus of this invention.

A block diagram representation of an embodiment 10 of the apparatus of this invention is shown in FIG. 1a. Referring to FIG. 1a, the embodiment 10 shown therein includes a source 20 of electromagnetic radiation, a first optical system 40, and an optical delivery system 30 for providing electromagnetic radiation from the source 20 to the first optical system 40. The first optical system 40 substantially collimates the provided electromagnetic radiation. This embodiment 10 also includes a sample holding assembly 50 for holding a microvolume liquid sample 60 and placing the microvolume liquid sample 60 in an optical path of the substantially collimated electromagnetic radiation, a filter assembly 70 including at least one filter, the filter assembly 70 being placed in the optical path of the substantially collimated electromagnetic radiation. The embodiment 10 shown in FIG. 1a also includes a second optical system 80 capable of receiving electromagnetic radiation transmitted through the sample and at least a portion of the sample holding assembly 50 and through the filter assembly 70, a detecting system 95 for detecting electromagnetic radiation, and an optical transmission system 90 for receiving electromagnetic radiation from the second optical system 80 and transmitting the received electromagnetic radiation to the detecting system 95. In the embodiment shown in FIG. 1a, the filter assembly 70 is located between the sample holding assembly 50 and the second optical system 80. In the embodiment shown in FIG. 1b, the filter assembly 70 is located between the sample holding assembly 50 and the first optical system 40.

The source 20 of electromagnetic radiation can be, but is not limited to, UV/Visible LED light source, a Xenon flash lamp, or a Deuterium lamp for UV and a tungsten source for visible. An optical delivery system 30 for providing electromagnetic radiation from the source 20 to the first optical system 40 can include, but is not limited to, a fiber optic path and optical components to focus the electromagnetic radiation from the source 20 onto the fiber in one embodiment, or, in another embodiment, an optical system including discrete optical components (such as, but not limited to, lenses, prisms, or/and mirrors) for transmitting the electromagnetic radiation from the source 20. The first optical system 40 can be, but is not limited to, a plano-convex lens that collimates electromagnetic radiation and directs it through the sample holding assembly 50 and the sample 60 or a collimating optical system to perform the same function. In some embodiments, the first optical system 40 can include optical components, such as, but not limited to, prisms or reflecting components, that redirect the collimated electromagnetic radiation. In those embodiments, the filter assembly 70 can be located within the first optical system 40 at a location wherein electromagnetic radiation is substantially collimated. In other embodiments, in which the optical delivery system 30 can include optical components, such as collimating components and collecting components, the filter assembly 70 can be located within the optical delivery system 30 at a location wherein electromagnetic radiation is substantially collimated. In similar embodiments, the filter assembly 70 can be located within the second optical system 80 or the optical transmission system 90 at a location wherein electromagnetic radiation is substantially collimated.

The sample holding assembly 50, in one embodiment, can include, but is not limited to, an assembly which has one or more of the following features: UV/visible transparent, abrasion-resistant, a optical-quality hydrophilic center (comprised of a material such as, but not limited to, Quartz glass or Polystyrene. The transmittance of the sample holding assembly 50 is selected to ensure that a measured signal remains within the limit of the linear absorbance range of the apparatus. In one aspect, the holding assembly 50 includes an abrasion-resistant hydrophobic surround (comprised of a material such as, but not limited to, Silicone, Fluorosilicone, Fluorosilane, Teflon emulsion or Teflon AF). In one aspect, the sample (e.g., a drop) is placed on a transparent center of the holding assembly 50 and substantially collimated electromagnetic radiation propagates through the transparent center and the sample. Other embodiments of the sample holding assembly 50 in which the sample is placed in an enclosed (or partially enclosed) holding assembly (such as, but not limited to, a microcuvette) are possible. In one embodiment of this invention includes, holding assemblies that do not substantially reflect or refract the substantially collimated electromagnetic radiation are utilized. One exemplary embodiment includes holding assemblies (such as, but not limited to, cuvettes, microcuvettes, or microcapillaries) having substantially planar surfaces and the substantially planar surfaces are substantially perpendicular to the collimated directed electromagnetic radiation.

The filter assembly 70 can include one or more filters. Embodiments with more than one filter assembly are also possible. The filters in the filter assembly 70 can be, but are not limited to, conventional electromagnetic (optical) filters, liquid crystal electronically adjustable filters, or thin film dielectric continuously tunable filter. The filter assembly 70 can be integral to apparatus or can be a removable filter assembly. Likewise, filters may be integral parts of or removable from the filter assembly 70. In one embodiment in which the filter assembly 70 includes more than one filter, the filter assembly 70 can be a group of filters 175 in a linear assembly (also referred herein as linear cartridge (160, FIG. 4)) or a "filter wheel" (150, FIG. 3). In another embodiment in which the filter assembly 70 includes more than one filter, a pre-selected filter from the filter assembly 70 may be placed in the optical path of collimated electromagnetic radiation by translating the filter assembly 70. The pre-selected filter substantially selects transmission in the predetermined wavelength region. The filters are pre-selected based on the desired sample to be measured and the width of the spectrum of the absorption (or emission) band arising from the interaction of electromagnetic radiation and the sample. In the exemplary, but not limiting, case of biological samples, electromagnetic radiation absorption is centered at wavelengths ($\lambda$) ranging from 200 nm to 800 nm, mostly at 230, 260 and 280 nm. The filter spectral band is selected to be centered at the desired wavelength and to have a width sufficient to span the width of the interaction spectral band of interest but narrow enough to exclude neighboring interaction spectral bands.

In the embodiment 10 (see FIGS. 1a and 1b) in which the filter assembly 70 includes more than one filter, the apparatus of this invention 10 can also include a positioning system 75 capable of placing the pre-selected filter in the optical path of the substantially collimated electromagnetic radiation. Such positioning system 75 can include electrical motors (for example, but not limited to, stepper motors, DC motors, linear motors; the motors can be direct drive or the positioning system can include coupling mechanisms to translate the motor motion to filter assembly motion), electrical motors with encoders, mechanical translation and detent mechanisms, or combinations thereof (such as electrical motors and mechanical detents and electromechanical release mechanisms). A variety of conventional detent mechanisms can be employed in the positioning system 75. The portion of the detent mechanism that is embedded in the filter assembly is schematically indicated by notches (170, FIGS. 3, 4). It should be noted that this indication is schematic and representative; any of the entire gamut of mechanical detent mechanism can be used. In the embodiments disclosed above, the filter assembly 70 could be removable by user.

It should also be noted that control of the translation, whether rotating the filter wheel (150, FIG. 3) to a predetermined position or translating the filter linear cartridge (160, FIG. 4) to a pre-determined position, may be accomplished under computer or processor control in some embodiments.

The second optical system 80 can be, but is not limited to, a lens that receives the electromagnetic radiation transmitted through the sample 60 and at least a portion of the sample holding assembly 50 and through the filter assembly 70 and couples the received electromagnetic radiation onto the optical transmission system 90. The optical transmission system 90, capable of receiving electromagnetic radiation from the second optical system 80 and transmitting the received electromagnetic radiation to the detecting system 95, can include, but is not limited to, a fiber optic path and optical components to image the transmitted electromagnetic radiation onto the detecting system 95, or, in another embodiment, an optical system including discrete optical components for receiving/transmitting the electromagnetic radiation and imaging the transmitted electromagnetic radiation onto the detecting system 95. The detecting system 95 can include, but is not limited to, photodiodes (one or more), diode array detectors and, depending on the desired measurement, photovoltaic (such as photodiodes), photoconductive or photoemissive detectors.

A schematic representation of another embodiment of the apparatus of this invention is shown in FIG. 2. Referring to FIG. 2, the embodiment 100 shown therein includes a source 20 of electromagnetic radiation, a first optical fiber 110 (including any optical components necessary to focus the electromagnetic radiation from the source 20 onto the fiber 110), a plano-convex lens 120 that collimates the electromagnetic radiation emanating from the fiber 110, a sample holding assembly 50 including a UV/visible transparent or semi-transparent, abrasion-resistant, optical-quality hydrophilic center 52 and an abrasion-resistant hydrophobic surround 54, a sample 60 disposed on the hydrophilic center 52 of the sample holding assembly 50, filter assembly 70, a lens 130 that receives the electromagnetic radiation transmitted through the sample 60 and at least a portion of the sample holding assembly 50 and through the filter assembly 70, a second optical fiber 140 that receives electromagnetic radiation from the lens 130 and transmits the received electromagnetic radiation, and a detecting system 95 (where the second optical fiber 140 includes any optical components to image the transmitted electromagnetic radiation onto the detecting system 95).

Figure 5:
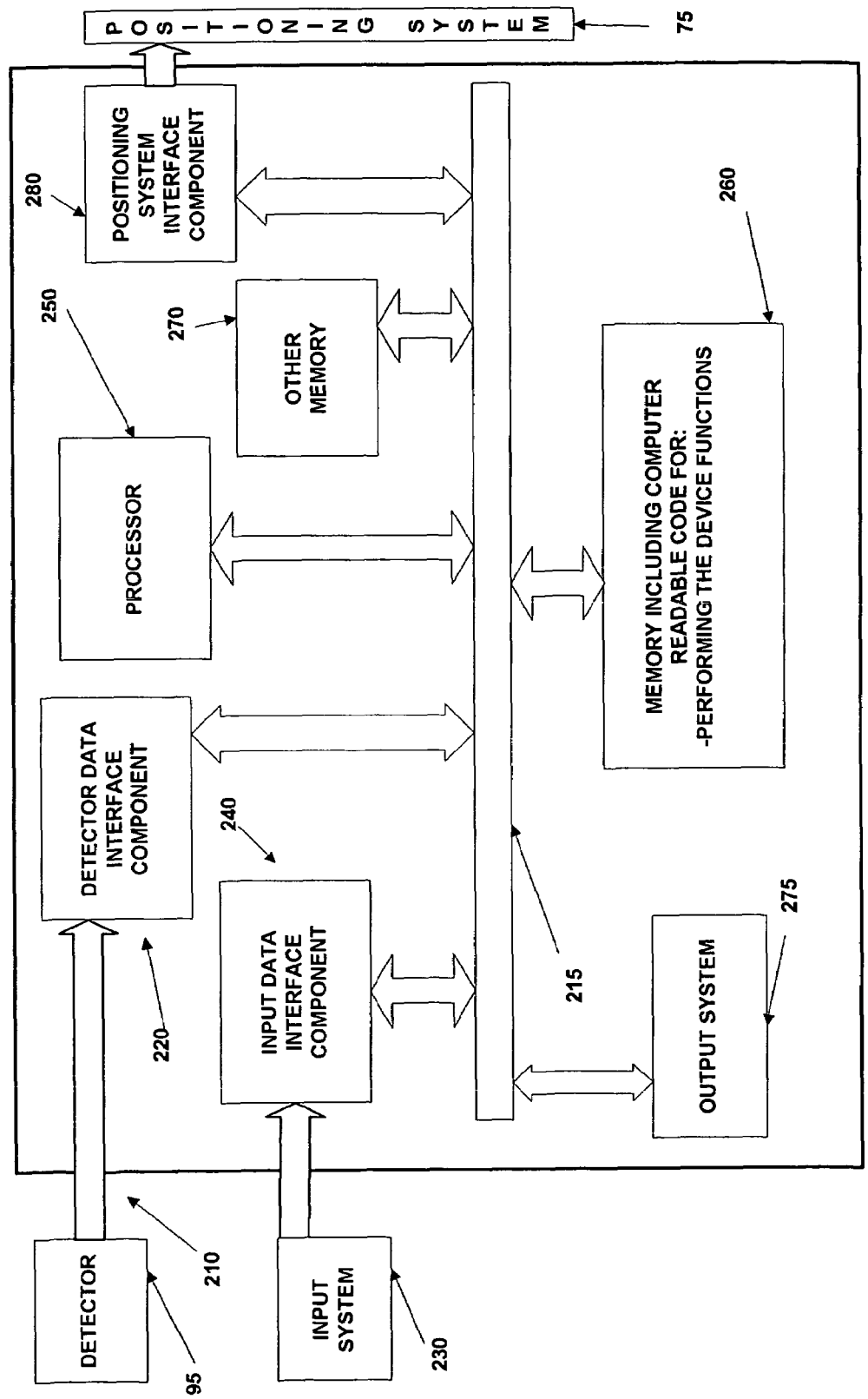
FIG. 5 is a block diagram representative of an embodiment of a portion of the apparatus of this invention.

An embodiment of the data collection and control portion 200 of the apparatus 10, 100 of this invention is shown, in block diagram form in FIG. 5. Referring to FIG. 5, the detector 95 is operatively connected to a data collector interface component 220 and is capable of providing a detector output signal 210 to the data collector interface component 220. An input system 230, capable of providing input instructions or, generally, data, is operatively connected to an input data interface component 240. The input system 230 can be, but is not limited to, a keyboard, a magnetic or optical disk drive or similar rotating memory device, a tape drive, another computer system, a voice input device, or an electronic tablet. The operative connection can be, but is not limited to, a wired, wireless, or network connection or a combination thereof. The data collection interface component 220 and the input data interface component 240 are operatively connected to a interconnection means 215 (such as, but not limited to, a common "bus"). One or more processors 250, a memory 260, another memory 270, one or more output devices 275, and a positioning system interface 280 are also operatively connected to the interconnection means 315. The positioning system interface 280 is operatively connected to the positioning system 75. The positioning system interface 280 is capable of providing control and positioning information to the positioning system 75.

The memory 360 has computer readable code embodied therein, the computer readable code capable of causing the one or more processors 310 to receive input data, select a predetermined filter from a number of filters based on the input data, and provide positioning information to the positioning system 75. The input data interface component 240, the input system 230 and the computer readable code (software) provide means for receiving data. In the embodiment in which the positioning system 75 includes electrical motors, the positioning information includes one or more electrical signals capable of causing one or more electrical motors to move the filter assembly 70 so that a pre-selected filter from the filter assembly 70 is placed substantially in the optical path of collimated electromagnetic radiation. In another embodiment, the computer readable code is also capable of causing the one or more processors 310 to receive data from the detector 95, calculate predetermined characteristics from the received detector data, organize the calculated predetermined characteristics in a predetermined ordering, and output the organized predetermined ordering to one or more output devices. The data collection interface component 220 and the computer readable code provide means for receiving detected data from the detector 95.

In one embodiment, the input data includes sample type (such as, but not limited to, type of biological sample) and/or desired wavelength (in another embodiment the desired wavelength can be calculated or obtained from a database or table), the detector data is utilized in calculating absorbance. In this embodiment, the desired ordering is in terms of wavelength and absorbance at that wavelength. The desired ordering is then outputted to one or more output devices. Embodiments of output devices include, but are not limited to, solid state memories, a magnetic or optical disk drives or similar rotating memory devices, tape drives, wired or wireless connections to another computer system, printers or display devices.

It should also be noted that other data collection and control for the apparatus (embodiment) 10 (or 100) could be performed by embodiment of the data collection and control portion 200 of the apparatus 10, 100 of this invention.

In general, the techniques described above may be implemented, for example, in hardware, software, firmware, or any combination thereof. The techniques described above may be implemented in one or more computer programs executing on a programmable computer including a processor, a storage medium readable by the processor (including, for example, volatile and non-volatile memory and/or storage elements), at least one input device, and at least one output device. Program code may be applied to data entered using the input device to perform the functions described and to generate output information. The output information may be applied to one or more output devices.

Elements and components described herein may be further divided into additional components or joined together to form fewer components for performing the same functions.

Each computer program within the scope of the claims below may be implemented in any programming language, such as assembly language, machine language, a high-level procedural programming language, or an object-oriented programming language. The programming language may be a compiled or interpreted programming language.

Each computer program may be implemented in a computer program product tangibly embodied in a computer-readable storage device for execution by a computer processor. Method steps of the invention may be performed by a computer processor executing a program tangibly embodied on a computer-readable medium to perform functions of the invention by operating on input and generating output.

Common forms of computer-readable or usable media include, for example, a floppy disk, a flexible disk, hard disk, magnetic tape, or any other magnetic medium, a CDROM, any other optical medium, punched cards, paper tape, any other physical medium with patterns of holes, a RAM, a PROM, and EPROM, a FLASH-EPROM, any other memory chip or cartridge, a carrier wave, or any other medium from which a computer can read.

Although the invention has been described with respect to various embodiments, it should be realized this invention is also capable of a wide variety of further and other embodiments within the spirit and scope of the appended claims.

What is claimed is:

1. An apparatus comprising:
   a source of electromagnetic radiation;
   a first optical system;
   an optical delivery system capable of providing electromagnetic radiation from said source to said first optical system;
   said first optical system being capable of substantially collimating the provided electromagnetic radiation;
   a sample holding assembly capable of holding a microvolume liquid sample and placing the microvolume liquid sample in an optical path of the substantially collimated electromagnetic radiation; the substantially collimated electromagnetic radiation also being transmitted through at least a portion of said sample holding assembly;
   a filter assembly comprising at least one filter, said filter assembly being positioned in the optical path of the substantially collimated electromagnetic radiation;
   a second optical system capable of receiving electromagnetic radiation transmitted through the sample and said at least a portion of said sample holding assembly and through said filter assembly;
   a detecting system capable of detecting electromagnetic radiation; and,
   an optical transmission system capable of receiving electromagnetic radiation from said second optical system and transmitting the received electromagnetic radiation to said detecting system;
   said second optical system being also capable of transmitting electromagnetic radiation to said optical transmission system; and
   said detecting system being optical disposed to receive electromagnetic radiation from said optical transmission system.

2. The apparatus of claim 1 wherein said filter assembly is located between said sample holding assembly and said second optical system.

3. The apparatus of claim 1 wherein said filter assembly is located between said sample holding assembly and said first optical system.

4. The apparatus of claim 1 wherein said filter assembly is a removable filter assembly.

5. The apparatus of claim 1 wherein said at least one filter comprises a plurality of filters.

6. The apparatus of claim 5 wherein said filter assembly comprises a fitter wheel.

7. The apparatus of claim 5 wherein said filter assembly comprises a filter linear cartridge.

8. The apparatus of claim 5 further comprising:
   a positioning system capable of placing a pre-selected filter from said plurality of filters in the optical path of the substantially collimated electromagnetic radiation.

9. The apparatus of claim 8 further comprising:
   an input system capable of providing input data;
   an input data interface component operatively connected to said input system and capable of receiving the input data;
   at least one processor;
   a positioning system interface component capable of providing positioning information to said positioning system; and at least one computer readable memory having computer readable code embodied therein, said computer readable code capable of causing said at least one processor to:
   receive the input data,
   select said predetermined filter based on the input data, and
   provide positioning information to said positioning system; said
   at least one processor said positioning system interface component and said input data interface component being operatively interconnected.

10. The apparatus of claim 9 further comprising:
    a data collector interface component operatively connected to said detector and capable of receiving input data;
    at least one output system;
    said data collector interface component and said at least one output system being operatively interconnected with said at least one processor, said positioning system interface component and said input data interface; and
    wherein said computer readable code is also capable of causing said at least one processor to:
    receive detected data from said detector,
    calculate predetermined characteristics from the received detected data,
    organize the calculated predetermined characteristics in a predetermined ordering, and
    output the organized predetermined ordering to said at least one output system.

11. A method for restricting, in an apparatus for measuring properties of microvolume liquid samples, transmission of electromagnetic radiation to a predetermined wavelength region, the method comprising the steps of:
    locating a pre-selected filter in an optical path of collimated electromagnetic radiation between a sample retaining assembly and an imaging optical system;
    the pre-selected filter being adjacent to the sample retaining assembly and to the imaging optical system; and
    whereby the pre-selected filter substantially restricts transmission to the pre-determined wavelength region.

12. The method of claim 11 further comprising the step of selecting one filter from a filter wheel; and, wherein the step of locating the pre-selected filter comprises the step of rotating the filter wheel to a pre-determined position.

13. The method of claim 11 further comprising the step of selecting one filter from a filter linear cartridge; and, wherein the step of locating a pre-selected filter comprises the step of translating the filter linear cartridge to a pre-determined position.

14. A method for restricting, in an apparatus for measuring properties of microvolume liquid samples, transmission of electromagnetic radiation to a predetermined wavelength region, the method comprising the steps of:
    locating a pre-selected filter in an optical path of collimated electromagnetic radiation between a transmission system capable of receiving electromagnetic radiation and directing it to a detecting system, and a sample retaining assembly capable of hold no a microvolume liquid sample and for placing the microvolume liquid sample in the optical path of collimated electromagnetic radiation;
    the pre-selected filter being adjacent to the sample retaining assembly and receiving electromagnetic radiation transmitted through the microvolume liquid sample; and
    whereby the pre-selected filter substantially restricts transmission to the pre-determined wavelength region.

15. The method of claim 14 further comprising the step of selecting one filter from a filter wheel; and, wherein the step of locating a pre-selected filter comprises the step of rotating the filter wheel to a pre-determined position.

16. The method of claim 14 further comprising the step of selecting one filter from a filter linear cartridge; and, wherein the step of placing a pre-selected filter comprises the step of translating the filter linear cartridge to a pre-determined position.

17. An apparatus comprising:
a source of electromagnetic radiation;
a first optical system;
means for providing electromagnetic radiation from said source to said first optical system;
said first optical system being capable of substantially collimating the provided electromagnetic radiation;
means for holding a microvolume liquid sample and for placing the microvolume liquid sample in an optical path of the substantially collimated electromagnetic radiation; the substantially collimated electromagnetic radiation also being transmitted through at least a portion of said holding means;
a filter assembly comprising at least one filter, said filter assembly being positioned in the optical path of the substantially collimated electromagnetic radiation;
a second optical system capable of receiving electromagnetic radiation transmitted through the sample and said at least a portion of said sample holding assembly and through said filter assembly;
means for detecting electromagnetic radiation; and,
means for receiving electromagnetic radiation from said second optical system and transmitting the received electromagnetic radiation to said detecting means;
said second optical system being also capable of transmitting electromagnetic radiation to said receiving/transmitting means; and
said detecting means being optical disposed to receive electromagnetic radiation from said receiving/transmitting means.

18. The apparatus of claim 17 wherein said filter assembly is located between said sample holding means and said second optical system.

19. The apparatus of claim 17 wherein said filter assembly is located between said sample holding means and said first optical system.

20. The apparatus of claim 17 wherein said filter assembly is a removable filter assembly.

21. The apparatus of claim 17 wherein said at least one filter comprises a plurality of filters.

22. The apparatus of claim 21 wherein said filter assembly comprises a filter wheel.

23. The apparatus of claim 21 wherein said filter assembly comprises a filter linear cartridge.

24. The apparatus of claim 21 further comprising:
means for placing a pre-selected filter from said plurality of filters in the optical path of the substantially collimated electromagnetic radiation.

25. The apparatus of claim 24 further comprising:
means for receiving input data;
means for selecting said predetermined filter based on the input data; and means for providing positioning information to said positioning system.

26. The apparatus of claim 25 further comprising:
at least one output system;
means for receiving detected data from said detector;
means for calculating predetermined characteristics from the received detected data;
means for organizing the calculated predetermined characteristics in a predetermined ordering; and
means for outputting the organized predetermined ordering to said at least one output system.

* * * * *